United States Patent [19]

Nyander et al.

[11] Patent Number: 5,223,591
[45] Date of Patent: Jun. 29, 1993

[54] INITIATORS FOR POLYMERIZATION

[75] Inventors: Johan Nyander, Sollentuna; Sonny Jönsson, Stockholm; Björn Elman; Ann-Britt Pettersson, both of Märsta; Per-Erik Sundell, Lidingö; Sven Göthe, Bromma; Jan-Erik Nyström, Kista, all of Sweden

[73] Assignee: Ciba-Geigy Corporation, Ardsley, N.Y.

[21] Appl. No.: 776,366

[22] PCT Filed: Mar. 20, 1990

[86] PCT No.: PCT/SE90/00179
§ 371 Date: Nov. 25, 1991
§ 102(e) Date: Nov. 25, 1991

[87] PCT Pub. No.: WO90/11303
PCT Pub. Date: Oct. 4, 1990

[30] Foreign Application Priority Data

Mar. 23, 1989 [SE] Sweden ................... 8901048

[51] Int. Cl.$^5$ .................... C08F 4/00; C07D 333/50
[52] U.S. Cl. ...................... 526/204; 549/29; 549/41; 549/49
[58] Field of Search ............. 526/204; 549/49, 41, 549/29

[56] References Cited

U.S. PATENT DOCUMENTS 4,407,759 10/1983 Crivello .................. 260/440
4,417,061 11/1983 Crivello .................. 549/3

FOREIGN PATENT DOCUMENTS 0297442 1/1989 European Pat. Off. .
2252765 10/1990 Japan .
75103903 9/1982 Sweden .

OTHER PUBLICATIONS

Morio et al., Journ. of Applied Polymer Sci.; 32:5727-5732 (1986); "Thermoinitiated Cationic Polymerization of Epoxy Resins by Sulfonium Salts".
Endo et al.; Journ. of Polymer Sci.: Polymer Letters Edition; 23:359-363 (1985); "Thermoinititated Cationic Polymerization of Bicyclo Ortho Ester by Benzylsulfonium Salts".
Asahi Denka Kogyo K. K.; Chemical Abstracts; 99(18) (1983) 141034v & JP 5837003.

Primary Examiner—Joseph L. Schofer
Assistant Examiner—Wu C. Cheng
Attorney, Agent, or Firm—Browdy and Neimark

[57] ABSTRACT

Initiators for cationic polymerization by thermal activation, photochemical activation (UV-irradiation) or activation by electron bombardment are compounds wherein a heterocyclic, aryl substituted or aryl ring is fused to a sulfonium moiety in combination with a non-nucleophilic anion. During the activation of the initiator, a carbon-sulfur bond is broken leading to formation of a sulfide and a carbonium ion within the same molecule. The carbonium ion initiates the polymerization.

13 Claims, No Drawings

INITIATORS FOR POLYMERIZATION

The present invention relates to the use of compounds as initiators for cationic polymerization by means of thermal activation or photochemical activation (UV-irradiation) or activation by electron bombardment (EB). The polymerization-initiator consists of a heterocyclic, arylsubstituted or with an arylring fused sulfonium salt in combination with a non-nucleophilic anion. During the activation of the initiator, a carbon-sulfur bond is broken leading to formation of a sulfide and a carbocation (carbenium ion) within the same molecule. The carbocation initiates the polymerization. Since the activation does not lead to fragmentation of the initiator-molecule into smaller molecules, no low molecular weight sulfur-containing decomposition products form that otherwise would evaporate or migrate from the polymer causing bad smell. The ring-opening cationic initiators in the present invention thereby possess great enviromental advantages both during the polymerization and in handling of the polymer products.

The present invention relates also to some compounds which are novel compounds per se.

BACKGROUND

Cationic polymerization (for a recent review of the area, see: Comprehensive Polymer Science 1989, 3, 579 ff), in contrast to radical polymerization, is not inhibited by the presence of oxygen in air and proceeds after UV-initiation in the dark. Cationic polymerization is also complementary to radical polymerization with respect to polymerizable monomers. Thus, electron rich carbon-carbon double bonds (e.g. alkenyl ethers) are easily cationically polymerized while acrylate monomers are usually unreactive. Vinyl ethers however, do not homopolymerize under radical polymerization conditions. Epoxides is another commercially important class of monomers that polymerize readily under cationic conditions but are inert to radical polymerization.

The utility of cationic polymerization has strongly been tempered by the fact that previously developed cationic initiators have inferior technical properties such as unsatisfactory high initiation temperature and poor solubility in monomer blends and smelly decomposition products.

Strong proton acids (e.g. $HClO_4$, $HBF_4$) or Lewis acids (e.g. $AlCl_3$, $BF_3$) initiate cationic polymerization of for example vinyl ethers and epoxides. These acids have a very limited utility in a technical context, such as curing of a coating, mainly due to the immediate polymerization that occurs upon mixing initiator and monomer, i.e. the system has no "pot life".

This problem has been circumvented by developing "latent proton acids". They are structurally recognized by being aryl-substituted "onium-salts", e.g. sulfonium-, iodonium-, or arsonium-salts, with non-nucleophilic anions such as $SbF_6^-$, $AsF_6^-$, $PF_6^-$, and $BF_4^-$. These salts are stable, latent sources of the corresponding strong Brönsteds acid $HSbF_6$, $HAsF_6$, and $HBF_4$ respectively, which are generated upon activation and initiate the polymerization. The salts are inactive until the activation occurs. A majority of this class of latent initiators require photochemical activation (irradiation by UV-light). (Belg. Pat. 828670, 1974; U.S. Pat. No. 3,981,897, 1976; Belg. Pat. 837782, 1970; Belg. Pat. 833472, 1976).

More recently, it has been shown that some sulfonium- and iodonium-salts can be thermally activated and utilized for the initiation of a cationic polymerization. Two methods for activation have been developed; redoxinitation (A. Ledwith, Polymer 1978, 19, 1217) and thermal initiation (Jap. Pat. 63.221.111, 1988, [CA 1989, 111, 40092y],; Jap. Pat. 63223002 1988 [CA 1989, 110, 173955h]; S. P. Pappas and L. W. Hill, J. Coating Technol., 1981, 53,43; S. P. Pappas and H. B. Feng, "Cationic Polymerization and Related Processes" ed. E. J. Goethals, Academic Press, New York, 1984; T. Endo and H. Uno, J. Polym. Sci., Polym. Lett. Ed., 1985, 23, 359; T. Endo and H. Arita, Makromol. Chem., Rapid Commun., 1985, 6, 137).

In common for these initiators is that the activation leads to a fragmentation, dissociation of the initiator molecule into decomposition products of lower molecular weight (e.g. sulfide) along with the initiation of a cationic polymerization, see figure.

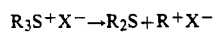

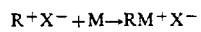

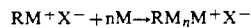

The deficiency of previously developed initiators (PDI) can thus be summarized in three points, where the present invention in all three aspects furnishes considerable improvements:

1. PDI have poor solubility in monomers which generally have a lipophilic character.
2. PDI yield low molecular decomposition products upon activation whose emission may cause enviromental problems. This is especially pronounced in the case of sulfonium salts where a low molecular sulfide is formed.
3. Commercially available initiators are limited to photochemical activation.

The activation of a thermal initiator involves a heterolytic cleavage of a carbon-sulfur bond to form the most stabilized carbocation. The activation temperature for an alkyl-substituted sulfonium salt strongly depends on the structure of the substituents. The activation temperature decreases if a more stabilized carbocation can be formed. Substituents of resonance stabilizing ability (e.g. benzylic and allylic) lower the temperature at which the cationic polymerization occurs. Electron-donating substituents (e.g. alkyl or alkoxy) in ortho or para positions at the benzylic group further decrease the activation temperature.

Besides controlling the initiation-temperature, the substituents have a strong influence on the solubility of the initiator-salt. Previously developed initiators have poor solubility in "solvent free" monomers such as epoxides, alkenyl ethers, or styrenes. This is due to the large polarity difference between the initiator and the monomer blend. Hydrophobic substituents such as longer n-alkyls can moderate the polar character of the initiator and improve its solubility properties in hydrophobic monomers.

Low molecular weight sulfides have a very strong and unpleasant smell even at very low concentration levels (ppm-levels). They are formed at the activation step and during the polymerization emission to the environment is very difficult to avoid. In addition, the remaining sulfide could at a later state migrate to the polymer surface and cause a smelly polymer film. It is therefore very important to structurally modify an initiator to avoid formation of low molecular weight sulfides.

The reaction scheme below illustrates the chemistry of a member of a previously developed initiator where tetrahydrothiophene is formed during the activation, followed by the initiation of a cationic polymerization of a vinyl ether.

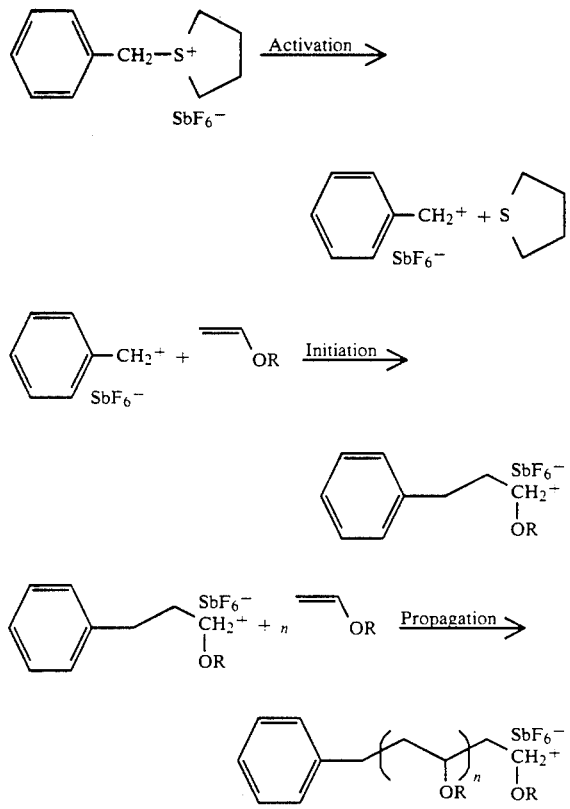

PRESENT INVENTION

The present invention relates to the use of compounds as initiators for cationic polymerization by means of thermal activation or photochemical activation (UV-irradiation) or activation by electron bombardment (EB). The polymerization-initiator consists of a heterocyclic, arylsubstituted or with an arylring fused sulfonium salt in combination with a non-nucleophilic anion. During the activation of the initiator, a carbon-sulfur bond is broken leading to formation of a sulfide and a carbocation (carbenium ion) within the same molecule. The carbocation initiates the polymerization. Since the activation does not lead to fragmentation of the initiator-molecule into smaller molecules, no low molecular weight sulfur-containing decomposition products from that otherwise would evaporate or migrate from the polymer causing bad smell. The ring-opening cationic initiators in the present invention thereby possess great enviromental advantages both during the polymerization and in handling of the polymer products.

According to to another aspect of the invention novel compounds are provided which are aryl substituted cyclic sulfonium salts of the structural formula

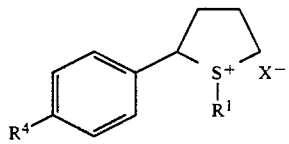

and which are selected from

S-methyl-2-phenyltetramethylenesulfonium hexafluoroantimonate,

S-methyl-2-phenyltetramethylenesulfonium hexafluorophosphate,

S-methyl-2-(p-tolyl)tetramethylenesulfonium hexafluoroantimonate,

S-methyl-2-(p-tolyl)tetramethylenesulfonium hexafluorophosphate,

S-methyl-2-(p-methoxyphenyl)tetramethylenesulfonium hexafluoroantimonate,

S-methyl-2-(p-methoxyphenyl)tetramethylenesulfonium hexafluorophosphate,

S-ethyl-2-phenyltetramethylenesulfonium tetrafluoroborate,

S-ethyl-2-(p-tolyl)tetramethylenesulfonium tetrafluoroborate,

S-(n-butyl)-2-phenyltetramethylenesulfonium hexafluorophosphate or

S-(n-butyl)-2-(p-methoxyphenyl)tetramethylenesulfonium hexafluorophosphate.

When using the compounds as initiators for cationic polymerization, the compounds are activated by electron bombardment (EB), UV-irradiation, or thermally, causing a ring-opening reaction. The resulting carbocation and sulfide will be within the same molecule and consequently, no low molecular degradation fragments will be formed:

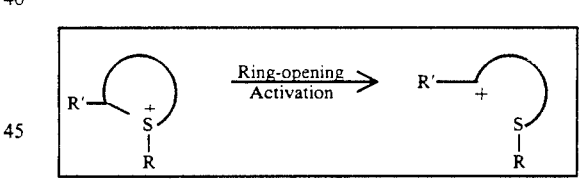

Great environmental advantages are achieved by using a ring-opening initiator, both during the polymerization and when handling the final product.

The reaction scheme below illustrates the activation of a ring-opening sulfonium salt with a non-nucleophilic anion according to this invention, followed by initiation and propagation of a cationic polymerization of a vinyl ether.

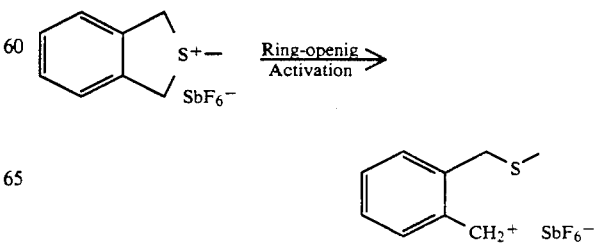

-continued

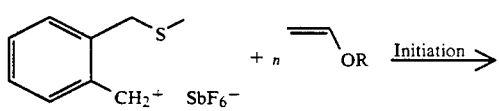

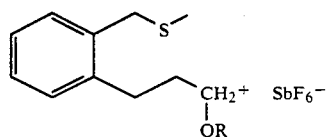

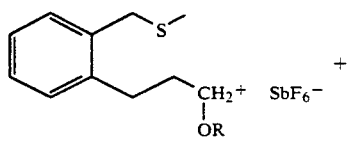

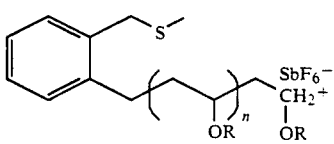

In order to keep the sulfide formed after activation within the cationic fragment, it is according to the present invention of great importance that:

i) The sulfonium salt is a heterocyclic, arylsubstituted or with an arylring fused, compound.

ii) The most stabilizing substituent at the sulfonium group is benzylic or substituted benzylic.

iii) The most stabilizing substituent is bonded to the sulfonium containing heterocycle in order to promote the ring-opening formation of the carbocation.

To efficiently promote a cationic polymerization it also necessary that the anion (counter ion) is non-nucelophilic and that the sulfonium salt is soluble in the monomer mixture.

Suitable compounds, polymerizable via a cationic polymerization, that can be used with ring-opening initiators according to the present invention are epoxides, alkenyl ethers, cyclic ethers, lactones, oxetanes, styrenes, vinylarenes, alicyclic vinyl compounds (e.g. vinylcyclohexane), spiro otho esters, spiro ortho carbonates, bicyclic ortho esters, isobutene, butadiene, isoprene, and phenol-formaldehyde resins.

The polymerization initiator according to the present invention is thus a heterocyclic, arylsubstituted or with an aryl-ring fused sulfonium salt in combination with a non-nucleophilic anion. Activation of the cyclic sulfonium salts according to present invention, is a ring-opening reaction forming a carbocation with a pendant sulfide group. Consequently, the sulfide will be covalently bonded to the initiating carbocationic fragment.

The polymerization initiator according to the present invention has one of the following structural formulae

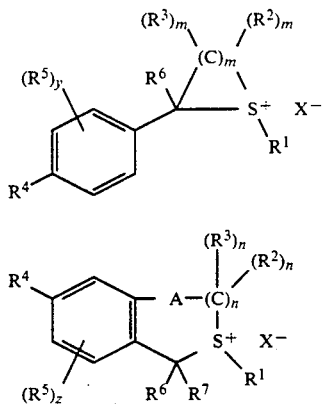

Structure I

Structure II wherein
m = an integer between 3 and 5
n = an integer between 1 and 3
z = an integer between 0 and 3
y = an integer between 0 and 4
X = represents a group of the formula $MY_r(1)$ or the formula $Q(2)$, wherein in where r is an integer between 4 and 6, examples of $MY_r(1)$ is $SbF_6$, $AsF_6$, $BF_4$, and $ClO_4$, the formula $Q(2)$ represents a sulfonic acid $R-SO_3$ wherein R is an alkyl or aryl group or a halogen-substituted, preferably F or Cl, alkyl or aryl group, examples of $Q(2)$ is $CF_3SO_3$ and $CH_3C_6H_4SO_3$, $R^1$ represents an alkyl or cycloalkyl group, preferably $C_1-C_{20}$, or an aryl group, $R^2$ represents hydrogen, an alkyl, alkenyl, cycloalkenyl or cycloalkyl group, preferably $C_1-C_{20}$, or aryl group, all $R^2$ being independent of each other, $R^3$ represents hydrogen, an alkyl, alkenyl, cycloalkenyl or cycloalkyl group, preferably $C_1-C_{20}$, or aryl group, all $R^3$ being independent of each other, $R^4$ represents hydrogen, halogen, an alkenyl, for instance a vinyl group, a cycloalkenyl, an alkyl or cycloalkyl group, preferably $C_1-C_{20}$, an alkoxy or thioalkoxygroup, preferably $C_1-C_{20}$, a hydroxyl- or alkyl($C_1-C_{12}$)terminated poly(alkyleneoxide) group with up to 10 alkyleneoxide units, an aryl group, an aryloxy or thioaryloxy group, $R^5$ represents halogen, an alkyl or cycloalkyl group, preferably $C_1-C_{20}$, an alkoxy or thioalkoxy group, preferably $C_1-C_{20}$, a hydroxyl- or alkyl($C_1-C_{12}$)terminated poly(alkyleneoxide) group with up to 10 alkyleneoxide units, an aryl group, an aryloxy or thioaryloxy group, wherein in structure I $R^4$ or $R^5$ (y=1-2) also can be the group

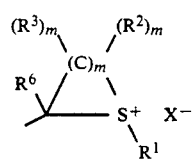

$R^6$ represents hydrogen, an alkyl, alkenyl, cycloalkenyl or cycloalkyl group, preferably $C_1-C_{20}$, or an aryl group, $R^7$ represents hydrogen, an alkyl, alkenyl, cycloalkenyl or cycloalkyl group, preferably $C_1-C_{20}$, or an aryl group, A represents

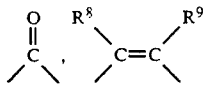

or a single bond, $R^8$ represents hydrogen, an alkyl or cycloalkyl group, preferably $C_1-C_{20}$, a hydroxyl- or alkyl($C_1-C_{12}$)terminated poly(alkyleneoxide) group with up to 10 alkyleneoxide units, an aryl group, an aryloxy or thioaryloxy group, $R^9$ represents hydrogen, an alkyl or cycloalkyl group, preferably $C_1-C_{20}$, a hydroxyl- or alkyl($C_1-C_{12}$)terminated poly(alkyleneoxide) group with up to 10 alkyleneoxide units, an aryl group, an aryloxy or thioaryloxy group, or $R^8$ and $R^9$ together form an aryl ring fused with the heterocyclic sulfonium ring, said aryl ring optionally being substituted with a group $R^{10}$ which can be a halogen atom, a nitro group, an alkyl or cycloalkyl group, preferably $C_1-C_{20}$, alkoxy or tihoalkoxy group, preferably $C_1-C_{20}$, a hydroxyl- or alkyl($C_1-C_{12}$)terminated poly(alkyleneoxide) group with up to 10 alkyleneoxide units, an aryl group, an aryloxy or thioaryloxy group.

Some initiators in the present invention are novel compounds per se while others are previously known compounds. The latter however, have not previously been described or suggested for use as polymerization-initiators. The compounds which are novel per se all have the general formula

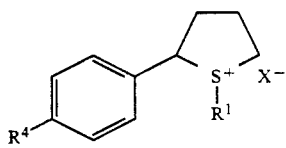

and are

S-methyl-2-phenyltetramethylenesulfonium hexafluoroaantimonate,
S-methyl-2-phenyltetramethylenesulfonium hexafluorophosphate,
S-methyl-2-(p-tolyl)tetramethylenesulfonium hexafluoroantimonate,
S-methyl-2-(p-tolyl)tetramethylenesulfonium hexafluorophosphate,
S-methyl-2-(p-methoxyphenyl)tetramethylenesulfonium hexafluoroantimonate,
S-methyl-2-(p-methoxyphenyl)tetramethylenesulfonium hexafluorophosphate,
S-ethyl-2-phenyltetramethylenesulfonium tetrafluoroborate,
S-ethyl-2-(p-tolyl)tetramethylenesulfonium tetrafluoroborate,
S-(n-butyl)-2-phenyltetramethylenesulfonium hexafluorophosphate or
S-(n-butyl)-2-(p-methoxyphenyl)tetramethylenesulfonium hexafluorophosphate.

EXAMPLES

The invention is further illustrated by the following examples which however are not intended to limit the scope of the invention in any respect.

Thermally induced cationic polymerisation

Two different difunctional cationically polymerizable monomers containing 1.0% by weight initiator were used. The initiator solutions were prepared by dissolving the initiator in the monomer.

Monomer 1 consists of triethyleneglycol divinylether, TEGDVE (GAF Chemical Corp.; DVE-3), with the following structure:

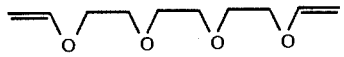

Monomer 2 consists of 3,4-epoxycyclohexylmethyl 3',4'-epoxycyclohexane carboxylate, EEC (Union Carbide; UVR 6110), with the following structure:

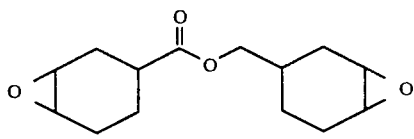

The polymerizations were studied with a Perkin-Elmer DSC-7, differential scanning calorimeter. The monomer/initiator solutions (3-5 mg) were sealed in aluminum pans before mounted into the calorimeter. The temperature scanning was 10° C./minute. The temperature range was 20°-225° C., depending on the type of initiator used. The DSC-thermograms generally showed a relatively sharp exothermic peak, resulting from the cationic polymerization initiated by the sulfonium salts. The results, peak temperature (Tp) and heat of polymerization ($-\Delta H$) are displayed in table 1. The peak temperature (Tp) is defined as the temperature at maximum heat flow and is approximatively the the temperature at which the activation and initiation occur. The variations in Tp (65°-157° C.) reflects the different ability of the substituents to promote ring-opening and to stabilize the initiating carbocation. $-\Delta H$ is the heat of reaction per mole of monomer. The heat of reaction/mole is a measure of the monomer-conversion. However, in order to adequately calculate the monomer-conversion a theoretical heat of reaction is required for these monomers at different temperatures, that is not available. The cured films are however hard and non-smelling, which are relevant technical criteria, so we conclude that 100% monomer-conversion corresponds to 150-160 kJ/mol at 120°-140° C. for TEGDVE

Comparative example 1

In this example monomer 1 (TEGDVE) and benzyltetramethylenesulfonium hexafluoroantimonate ($BTMS^+SbF_6^-$) were used. This compound is a good representative for previously developed initiators (J. Polym. Sci., Polym. Lett. Ed., 1985, 23, 359). The initiator is thermally cleaved according to the equation below:

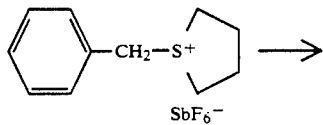

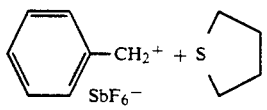

A hard crosslinked polymer was found, but a strong odour of tetrahydrothiophene was noticable when opening the aluminium pans. Tp and —ΔH are shown in table 1.

Comparative example 2

For this comparison, monomer 2(EEC) and BTMS+SbF$_6^-$, the same sulfonium salt initiator as in comparative example 1, were used. The thermally induced cleavage proceeds as described in comparative example 1. A hard crosslinked polymer was found, but a strong odour of tetrahydropthiophene was noticable when opening the aluminium pans.

In the following examples different sulfonium salts of the structures I and II according to the present invention were used as cationic initiators. The sulfonium salts were all synthesized according to the procedures presented in experimentals. In all polymerization studies, where different but analogous structures of I and II were examined, hard and crosslinked polymers were found. However, no detectable odour from organic sulfides or sulfur containing compounds were observed when opening the aluminium pans. Tp and —ΔH are shown in table 1.

EXAMPLE 1

TEGDVE was used as monomer. S-Methyl-2-phenyltetramethylenesulfonium hexafluoroantimonate according to structure A1 (below) was used as initiator. Tp and —ΔH are shown in table 1.

EXAMPLE 2

EEC was used as monomer. S-Methyl-2-phenyltetramethylenesulfonium hexafluoroantimonate according to structure A1 (below) was used as initiator. Tp and —ΔH are shown in table 1.

EXAMPLE 3

TEGDVE was used as monomer. S-Methyl-2-phenyltetramethylenesulfonium hexafluorophosphate according to structure A2 (below) was used as initiator. Tp and —ΔH are shown in table 1.

EXAMPLE 4

EEC was used as monomer. S-Methyl-2-phenyltetramethylenesulfonium hexafluorophosphate according to structure A2(below) was used as initiator. Tp and —ΔH are shown in table 1.

EXAMPLE 5

TEGDVE was used as monomer. S-Methyl-2-(p-tolyl)tetramethylenesulfonium hexafluoroantimonate according to structure A3 (below) was used as initiator. Tp and —ΔH are shown in table 1.

EXAMPLE 6

EEC was used as monomer. S-Methyl-2-(p-tolyl)tetramethylenesulfonium hexafluoroantimonate according to structure A3 (below) was used as initiator. Tp and —ΔH are shown in table 1.

EXAMPLE 7

TEGDVE was used as monomer. S-Methyl-2-(p-tolyl)tetramethylenesulfonium hexafluorophosphate according to structure A4 (below) was used as initiator. Tp and —ΔH are shown in table 1.

EXAMPLE 8

TEGDVE was used as monomer. S-Methyl-2-(p-methoxyphenyl)tetramethylenesulfonium hexafluoroantimonate according to structure A5(below) was used as initiator. Tp and —ΔH are shown in table 1.

EXAMPLE 9

EEC was used as monomer. S-Methyl-2-(p-methoxyphenyl)tetramethylenesulfonium hexafluoroantimonate according to structure A5(below) was used as initiator. Tp and —ΔH are shown in table 1.

EXAMPLE 10

TEGDVE was used as monomer. S-Methyl-2-(p-methoxyphenyl)tetramethylenesulfonium hexafluorophosphate according to structure A6 (below) was used as initiator. Tp and —ΔH are shown in table 1.

EXAMPLE 11

EEC was used as monomer. S-Methyl-2-(p-methoxyphenyl)tetramethylenesulfonium hexafluorophosphate according to structure A6 (below) was used as initiator. Tp and —ΔH are shown in table 1.

EXAMPLE 12

TEGDVE was used as monomer. S-ethyl-2-phenyltetramethylenesulfonium tetrafluoroborate according to structure A7 (below) was used as initiator. Tp and —ΔH are shown in table 1.

EXAMPLE 13

TEGDVE was used as monomer. S-ethyl-2-(p-tolyl)-tetramethylenesulfonium tetrafluoroborate according to structure A8 (below) was used as initiator. Tp and —ΔH are shown in table 1.

EXAMPLE 14

TEGDVE was used as monomer. S-(n-butyl)-2-phenyltetramethylenesulfonium hexafluorophosphate according to structure A9 (below) was used as initiator. Tp and —ΔH are shown in table 1.

EXAMPLE 15

TEGDVE was used as monomer. S-(n-butyl)-2-(p-methoxyphenyl)tetramethylenesulfonium hexafluorophosphate according to structure A10 (below) was used as initiator. Tp and —ΔH are shown in table 1.

EXAMPLE 16

TEGDVE was used as monomer. 2-Methyl-1,3-dihydroisothianaphthenium hexafluoroantimonate according to structure B1 (below) was used as initiator. Tp and —ΔH are shown in table 1.

EXAMPLE 17

TEGDVE was used as monomer. 2-Ethyl-1,3-dihydroisothianaphthenium tetrafluoroborate according to structure B2 (below) was used as initiator. Tp and —ΔH are shown in table 1.

EXAMPLE 18

TEGDVE was used as monomer. S-Methyl-2-(E-2-phenylethenyl)-[3,4]-benzo-2,5-dihydrothiophenium hexafluorophosphate according to structure B3 (below) was used as initiator. After dissolving the initiator B3 into the monomer, the polymerization started within 10 minutes.

EXAMPLE 19

TEGDVE was used as monomer. S-Methyl-[3,4]-benzo-5-phenyl-2,7-dihydrothiepinium hexafluorophosphate according to structure C1 (below) was used as initiator. Tp and $-\Delta H$ are shown in table 1.

EXAMPLE 20

TEGDVE was used as monomer. 2-Ethyl-4-oxoisothiochromanium tetrafluoroborate according to structure D1 (below) was used as initiator. Tp and $-\Delta H$ are shown in table 1.

Structure A1-A10:

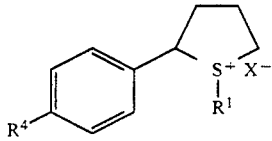

| Structure | R$^1$ | R$^4$ | X$^-$ |
|---|---|---|---|
| A1 | CH$_3$ | H | SbF$_6^-$ |
| A2 | CH$_3$ | H | PF$_6^-$ |
| A3 | CH$_3$ | CH$_3$ | SbF$_6^-$ |
| A4 | CH$_3$ | CH$_3$ | PF$_6^-$ |
| A5 | CH$_3$ | OCH$_3$ | SbF$_6^-$ |
| A6 | CH$_3$ | OCH$_3$ | PF$_6^-$ |
| A7 | CH$_2$CH$_3$ | H | BF$_4^-$ |
| A8 | CH$_2$CH$_3$ | CH$_3$ | BF$_4^-$ |
| A9 | n-C$_4$H$_9$ | H | PF$_6^-$ |
| A10 | n-C$_4$H$_9$ | OCH$_3$ | PF$_6^-$ |

Structure B1-B3:

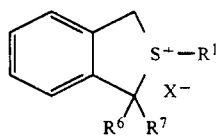

| Structure | R$^1$ | R$^6$ | R$^7$ | X$^-$ |
|---|---|---|---|---|
| B1 | CH$_3$ | H | H | SbF$_6^-$ |
| B2 | CH$_2$CH$_3$ | H | H | BF$_4^-$ |
| B3 | CH$_3$ | CHCHC$_6$H$_5$ | H | PF$_6^-$ |

Structure C1:

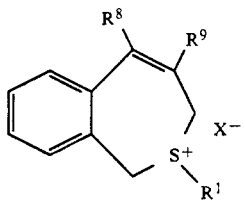

| Structure | R$^1$ | R$^8$ | R$^9$ | X$^-$ |
|---|---|---|---|---|
| C1 | CH$_3$ | Ph | H | PF$_6^-$ |

Structure D1:

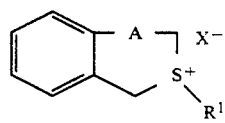

| Structure | R$^1$ | A | X$^-$ |
|---|---|---|---|
| D1 | CH$_2$CH$_3$ | O=C | BF$_4^-$ |

TABLE 1

DSC-results from thermally induced cationic polymerizations

| Example | Initiator | Monomer | Tp (°C) | $-\Delta H$ (kJ/mol) |
|---|---|---|---|---|
| Compar. ex. 1 | BTMS$^+$SbF$_6^-$ | TEGDVE | 121.9 | 152.0 |
| Compar. ex. 2 | BTMS$^+$SbF$_6^-$ | EEC | 147.8 | 142.4 |
| 1 | A1 | TEGDVE | 124.9 | 159.7 |
| 2 | A1 | EEC | 135.6 | 107.5 |
| 3 | A2 | TEGDVE | 128.1 | 142.9 |
| 4 | A2 | EEC | 157.3 | 57.6 |
| 5 | A3 | TEGDVE | 103.2 | 155.1 |
| 6 | A3 | EEC | 123.2 | 134.3 |
| 7 | A4 | TEGDVE | 122.5 | 137.4 |
| 8 | A5 | TEGDVE | 69.0 | 125.4 |
| 9 | A5 | EEC | 91.8 | 127.1 |
| 10 | A6 | TEGDVE | 65.5 | 127.0 |
| 11 | A6 | EEC | 87.0 | 41.9 |
| 12 | A7 | TEGDVE | 139.3 | 140.5 |
| 13 | A8 | TEGDVE | 134.6 | 150.2 |
| 14 | A9 | TEGDVE | 141.2 | 136.7 |
| 15 | A10 | TEGDVE | 77.3 | 127.8 |
| 16 | B1 | TEGDVE | 147.7 | 144.4 |
| 17 | B2 | TEGDVE | 146.9 | 139.8 |
| 19 | C1 | TEGDVE | 141.7 | 142.0 |
| 20 | D1 | TEGDVE | 121.1 | 136.1 |

The peak temperature (Tp) is defined as the temperature at maximum heat flow and $-\Delta H$ is the heat of reaction per mole of monomer.

UV-initiated cationic polymerization

EXAMPLE 21

The polymerization was studied by the use of a Perkin-Elmer DSC-7 differential scanning calorimeter, equipped with a DPA-7 double beam photocalorimetric accessory including a 200 W high-pressure Mercury-Xenon lamp (Hanovia 901-B0011). 1,0% by weight of the initiator 2-ethyl-4-oxoisothiochromanium tetrafluoroborate, according to structure D1, was dissolved in TEGDVE. 2-3 mg of the solution was placed in an aluminium pan, which was then mounted into the DSC. The sample was irradiated isothermally at 20° C. for 4 minutes by the use of the lamp described above. The results from the exothermal cationic polymerization were: irradiation time to maximum heat flow ($t_p$) was 0.86 min and heat of polymerization ($-\Delta H$) was 106.4 kJ/mol. A hard crosslinked polymer was found. No detectable odour from any organic sulfide or sulfur containing compound was noticed during or after the polymerization.

Electron beam (EB) initiated cationic polymerization

Solutions were made by dissolving 0,75% (w/w) initiator in mixtures 90% (w/w) TEGDVE and 10% (w/w) CAB (cellulose acetate butyrate; thickener).

Samples were coated on polyethylene sheets and irradiated under a nitrogen atmosphere, using a Energy Sciences Electrocurtain. Applied dose was 1 Mrad.

Comparative example 3

BTMS$^+$SbF$_6^-$, the same sulfonium salt initiator as in comparative examples 1 and 2 was used. A hard crosslinked polymer was found, but a strong odour of tetrahydrothiophene was noticable

EXAMPLE 22

2-Methyl-1,3-dihydroisothianaphthenium hexafluoroantimonate according to structure B1 was used as initiator. A hard crosslinked polymer was found, and no detectable odour from organic sulfides or sulfur containing compounds was observed Solubility test In order to demonstrate the enhanced solubility of the initiators used according to the present invention compared to previously developed initiators, a less polar (more hydrophobic) monomer than TEGDVE was chosen, namely cyclohexyl vinyl ether (CHVE). In the two examples below, the sulfonium salts have the same anion (PF$_6^-$).

Comparative example 4

BTMS$^+$PF$_6^-$ (J. Polym. Sci., Polym. Lett. Ed., 1985, 23, 359) was very poorly soluble in CHVE (80% w/w in acetone).

EXAMPLE 23

An 1% (w/w) homogeneous solution of initiator A9 was easily obtained in CHVE (80% w/w in acetone).

EXPERIMENTAL

Many different sulfonium salts of the general structures I and II according to present invention, were synthesized and characterized.

Nuclear Magnetic Resonans (NMR) spectra were recorded on a 200 MHz Bruker AC200 spectrometer. The chemical shifts are given in ppm˙ ($\delta$) relative to tetramethylsilane (internal standard). Melting points were recorded on a Perkin-Elmer DSC-7 differential scanning calorimeter and UV-absorption spectra were recorded with a Perkin-Elmer Lambda 17 UV/VIS spectrometer. All chemicals were purchased from Aldrich Chemical Co.

S-Methyl-2-phenyltetramethylenesulfonium hexafluoroantimonate (A1)

To a solution of 2-phenyltetrahydrothiophene (1,632 g, 10 mmol) (a general procedure for synthesis of 2-aryltetrahydrothiophenes was applied: D. L. Tuleen and R. H. Bennett, J. Heterocyclic Chem., 1969, 6, 115) in 4 ml acetonitrile was methyl iodide (2.129 g, 15 mmol) added at ambient temperature. After 24 the solvent was evaporated and 20 ml of water was added. The water phase was washed with diethyl ether several times to remove unreacted starting material. NaSbF$_6$ (2.587 g, 10 mmol) was added. A yellow oil separated, which was extracted to a CH$_2$Cl$_2$ phase. The CH$_2$Cl$_2$ phase was washed with an aqueous solution of Na$_2$SO$_3$ and water respectively and then dried with MgSO$_4$. Evaporation yielded 63% of the desired product A1 as a mixture of two diastereomers. $^1$H-NMR (acetone-d$_6$) $\delta$ 7.4–7.7 (10 H, m, Ph-H), 5.63 (1 H, dd, J=5.7 and 12.0 Hz, >S$^+$—CH—), 5.32 (1 H, dd, J=6.4 and 9.7 Hz, >S$^+$—CH—), 4.0–4.3 (2 H, m, >S$^+$—CH$_2$—), 3.6–3.9 (2 H, m, >S$^+$—CH$_2$—), 3.32 (3 H, s, >S$^+$—CH$_3$), 2.56 (3 H, s, >S$^+$—CH$_3$), 2.4–3.2 (8 H, m, >S$^+$—CH$_2$—CH$_2$—CH$_2$—); Anal. Calcd for C$_{11}$H$_{15}$F$_6$SSb: C, 31.8%; H, 3.6%; S, 7.7%. Found: C, 32.7%; H, 3.8%; S, 8.7%.

S-Methyl-2-phenyltetramethylenesulfonium hexafluorophosphate (A2)

This compound was synthesized according to the procedure described for A1, but NaSbF$_6$ was replaced by KPF$_6$ (1.841 g, 10 mmol). A slowly crystallizing oil of the diastereomeric mixture of A2 was obtained in 67% yield. $^1$H-NMR (acetone-d$_6$) $\delta$ 7.4–7.7 (10 H, m, Ph-H), 5.61 (1 H, dd, J=5.7 and 11.9 Hz, >S$^+$—CH—), 5.31 (1 H, dd, J=6.4 and 9.7 Hz, >S$^+$—CH—), 4.0–4.3 (2 H, m, >S$^+$—CH$_2$—), 3.6–3.9 (2 H, m, >S$^+$—CH$_2$—), 3.29 (3 H, s, >S$^+$—CH$_3$), 2.54 (3 H, s, >S$^+$—CH$_3$), 2.4–3.0 (8 H, m, >S$^+$—CH$_2$—CH$_2$—CH$_2$—).

S-Methyl-2-(p-tolyl)tetramethylenesulfonium hexafluoroantimonate (A3)

This compound was synthesized according to the procedure described for A1 starting from 1.773 g (10 mmol) of 2-p-tolyltetrahydrothiophene. A slowly crystallizing oil of the diastereomeric mixture of A3 was obtained in 77% yield. $^1$H-NMR (acetone-d$_6$) $\delta$ 7.46–7.53 (4 H, m, Ar—H), 7.27–7.37 (4 H, m, Ar—H), 5.57 (1 H, dd, J=5.8 and 11.9 Hz, >S$^+$—CH—), 5.27 (1 H, dd, J=6.3 and 9.6 Hz, >S$^+$—CH—), 4.0–4.2 (2 H, m, >S$^+$—CH$_2$—), 3.6–3.9 (2 H, m, >S$^+$—CH$_2$—), 3.28 (3 H, s, >S$^+$—CH$_3$), 2.53 (3 H, s, >S$^+$—CH$_3$), 2.38 (3 H, s, Ar—CH$_3$), 2.35 (3H, s, Ar—CH$_3$), 2.3–3.0 (8 H, m, >S$^+$—CH$_2$—CH$_2$—CH$_2$—); Anal. Calcd for C$_{12}$H$_{17}$F$_6$SSb: C, 33.6%; H, 4.0%; S, 7.5%. Found: C, 34.6%; H, 3.9%; S, 7.9%.

S-Methyl-2-(p-tolyl)tetramethylenesulfonium hexafluorophosphate (A4)

This compound was synthesized according to the procedure described for A1. The starting material was 1.773 g (10 mmol) of 2-(p-tolyl)tetrahydrothiophene but NaSbF$_6$ was replaced by KPF$_6$ (1.841 g, 10 mmol). A lightly yellow oil of a diastereomeric mixture of A4 was obtained in 65% yield. $^1$H-NMR (acetone-d$_6$) 7.43–7.56 (4 H, m, Ar—H), 7.23–7.43 (4 H, m, Ar—H), 5.60 (1 H, dd, J=5.8 and 11.9 Hz, >S$^+$—CH—), 5.48 (1 H, dd, J=6.3 and 9.6 Hz, >S$^+$—CH—), 3.96–4.21 (2 H, m, >S$^+$—CH$_2$—), 3.56–3.90 (2 H, m, >S$^+$—CH$_2$—), 3.24 (3 H, s, >S$^+$—CH$_3$), 2.53 (3 H, s, >S$^+$—CH$_3$), 2.39 (3 H, s, Ar—CH$_3$), 2.39 (3 H, s, Ar—Ch$_3$), 2.2–3.0 (8H, m, >S$^+$—CH$_2$—CH$_2$—CH$_2$—)

S-Methyl-2-(p-methoxyphenyl)tetramethylenesulfonium hexafluoroantimonate (A5)

This compound was synthesized according to the procedure described for A1 starting from 1.933 g (10 mmol) of 2-(p-methoxyphenyl)tetrahydrothiophene. A yellow oil of the diastereomeric mixture of A5 was obtained in 47% yield. $^1$H-NMR (acetone-d$_6$) $\delta$ 7.5–7.6 (4 H, m, Ar—H), 6.9–7.1 (4 H, m, Ar—H), 5.63 (1 H, dd, J=5.6 and 12.1 Hz, >S$^+$—CH—), 5.32 (1 H, dd, J=6.4 and 9.5 Hz, >S$^+$—CH—), 4.0–4.3 (2 H, m, >S$^+$—CH$_2$—), 3.85 (3 H, s, —O—CH$_3$), 3.83 (3 H, s, —O—CH$_3$), 3.6–3.9 (2 H, m, >S$^+$—CH$_2$—), 3.28 (3 H, s, >S$^+$—CH$_3$), 2.55 (3 H, s, >S$^+$—CH$_3$), 2.3–3.1 (8 H, m, >S$^+$—CH$_2$—CH$_2$—CH$_2$—); Anal. Calcd for C$_{12}$H$_{17}$F$_6$SSb: C, 32.4%; H, 3.9%; S, 7.2%. Found: C, 33.8%; H, 3.9%; S, 7.4%.

S-Methyl-2-(p-methoxyphenyl)tetramethylenesulfonium hexafluorophosphate (A6)

This compound was synthesized according to the procedure described for A1. The starting material was 1.933 g (10 mmol) of 2-(p-methoxyphenyl)tetrahydrothiophene, but $NaSbF_6$ was replaced by $KPF_6$ (1.841 g, 10 mmol). A yellow oil of a diastereomeric mixture of A6 was obtained in 71% yield. $^1$H-NMR (acetone-$d_6$) δ 7.5–7.6 (4 H, m, Ar—H), 6.9–7.1 (4 H, m, Ar—H), 5.63 (1 H, dd, J=5.6 and 12.1 Hz, >S$^+$—CH—), 5.32 (1 H, dd, J=6.4 and 9.5 Hz, >S$^+$—CH—), 4.0–4.3 (2 H, m, >S$^+$—CH$_2$—), 3.85 (3 H, s, —O—CH$_3$), 3.83 (3 H, s, —O—CH$_3$), 3.6–3.9 (2 H, m, >S$^+$—CH$_2$—), 3.28 (3 H, s, >S$^+$—CH$_3$), 2.55 (3 H, s, >S$^+$—CH$_3$), 2.3–3.1 (8 H, m, >S$^+$—CH$_2$—CH$_2$—CH$_2$—).

S-Ethyl-2-phenyltetramethylenesulfonium tetrafluoroborate (A7)

2-Phenyltetrahydrothiophene (1.632 g, 10 mmol) (J. Heterocyclic Chem., 1969, 6, 115) was dissolved in 10 ml of dry $CH_2Cl_2$ at 0° C. To this solution, which was kept under $N_2$, 10 ml of triethyloxonium tetrafluoroborate (10 mmol; 1M solution in $CH_2Cl_2$) was added. Then the reaction mixture was stirred for 5 h at ambient temperature. Evaporation of solvent gave an oil that was washed with diethyl ether several times. After dissolving the oil in $CH_2Cl_2$ the organic phase was washed with water, dried with $MgSO_4$ and evaporated. A yellow oil was obtained in 76% yield as a 2.4/1 mixture of two diastereomers of A7. $^1$H-NMR (acetone-$d_6$) δ 7.8–7.4 (5 H, m, Ph-H), 5.7–5.3 (1 H, >S$^+$—CH—), including 5.64 (dd, J=5.4 and 12.4 Hz, minor isomer) and 5.38 (dd, J=6.4 and 10.1 Hz, major isomer)), 4.2–3.0 (4 H, m, >S$^+$—CH$_2$—), 3.0–2.4 (4 H, m, >S$^+$—CH$_2$—CH$_2$—CH$_2$—), 1.55 (t, J=7.4 Hz, CH$_3$ is major isomer), 1.01 (t, J=7.4 Hz, CH$_3$ in minor isomer).

S-Ethyl-2-(p-tolyl)tetramethylenesulfonium tetrafluoroborate (A8)

Triethyloxonium tetrafluoroborate 10 ml (10 mmol; 1M solution in $CH_2Cl_2$) was added to a 10 ml dry solution of 1.773 g (10 mmol) of 2-(p-tolyl)tetrahydrothiophene in $CH_2Cl_2$ according to the procedure described for A7. A yellow oil of a diastereomeric mixture of A8 was obtained in 76% yield. $^1$H-NMR (acetone-$d_6$) δ 7.52–7.56 (4 H, m, Ar—H), 7.28–7.37 (4 H, m, Ar—H), 5.64 (1 H, dd, J=5.8 and 11.8 Hz, >S$^+$—CH—), 5.37 (1 H, dd, J=6.3 and 9.9 Hz, >S$^+$—CH—), 4.0–4.2 (2 H, m, >S$^+$—CH$_2$—CH$_2$—), 3.6–3.9 (2 H, m, >S$^+$—CH$_2$—CH$_2$—), 3.65 (2 H. q, >S$^+$—CH$_2$—CH$_3$), 2.35–3.25 (10 H, m, >S$^+$—CH$_2$—CH$_2$—CH$_2$—, >S$^+$—CH$_2$—CH$_3$), 2.37 (3H, s, Ar—CH$_3$), 2.34 (3H, s, Ar—CH$_3$), 1.51 (3 H, t, J=7.4 Hz, >S$^+$—CH$_2$—CH$_3$, 1.00 (3H, t, J=7.4 Hz, >S$^+$—CH$_2$—CH$_3$).

S-(n-Butyl)-2-phenyltetramethylenesulfonium hexafluorophosphate (A9)

2-(p-tolyl)tetrahydrothiophene (1.773 g, 10 mmol) was alkylated with 1-butyl iodide (2.76 g, 15 mmol) according to the procedure described for compound A1 but $NaSbF_6$ was replaced by $KPF_6$ (1.841 g, 10 mmol). A lightly yellow oil of a diastereomeric mixture of A9 was obtained in 25% yield. $^1$H-NMR (acetone-$d_6$) 7.4–7.8 (10 H, m, Ph-H), 5.69 (1 H, dd, >S$^+$—CH—), 5.43 (1 H, dd, >S$^+$—CH—), 3.5–4.2 (8 H, m, >S$^+$—CH$_2$—), 2.40–3.25 (8 H, m, >S$^+$—CH$_2$—CH$_2$—CH—), 1.15–2.0 (8 H, m, CH$_3$—CH$_2$—CH$_2$—), 0.91 (3 H, t, CH$_3$—), 0.73 (3 H, t, CH$_3$—).

S-(n-Butyl)-2-(p-methoxyphenyl)tetramethylenesulfonium hexafluorophosphate (A10)

This compound was synthesized according to the procedure described for A1. The starting material was 1.933 g (10 mmol) of 2-(p-methoxyphenyl)tetrahydrothiophene and 2.76 g (15 mmol) of 1-butyl iodide. Instead of $NaSbF_6$ 1.841 g (10 mmol) of $KPF_6$ was used. A lightly yellow oil of a diastereomeric mixture of A10 was obtained in 21% yield. $^1$H-NMR (acetone-$d_6$) δ 7.55–7.67 (4 H, m, Ar—H), 6.98–7.13 (4 H, m, Ar—H), 5.65 (1 H, dd, J=5.5 and 12.2 Hz, >S$^+$—CH—), 5.38 (1 H, dd, J=6.5 and 10.7 Hz, >S$^+$—CH—), 3.5–4.2 (8 H, m, >S$^+$—CH$_2$—), 3.86 (3 H, s, Ar—CH$_3$), 3.84 (3 H, s, Ar—CH$_3$), 2.40–3.25 (8 H, m, >S$^+$—CH$_2$—CH$_2$—CH—), 1.15–2.0 (8 H, m, CH$_3$—CH$_2$—CH$_2$—), 0.93 (3 H, t, CH$_3$—), 0.76 (3 H, t, CH$_3$—).

2-Methyl-1,3-dihydroisothianaphthenium hexafluoroantimonate (B1)

To 1,3-dihydroisothianaphthene (1.326 g, 10 mmol) (J. A. Oliver and P. A. Ongley, Chem. Ind. (London), 1965, 1024) dissolved in 3 ml of acetone was added 2.129 g (15 mmol) methyl iodide under $N_2$ at ambient temperature. After 24 h of stirring the solvent was evaporated. The residue was washed with diethyl ether to remove unreacted starting material, giving white crystals of 2-methyl-1,3-dihydroisothianaphthenium iodide 2.251 g (81%).

To a well stirred solution of 20 ml of ethanol kept at ambient temperature 0.319 g (1.86 mmol) of $AgSbF_6$ and 0.259 g (1.86 mmol) of 2-methyl-1,3-dihydroisothianaphthenium iodide was added. After 2 h 0.214 g of AgI (s) could be filtered off. Evaporation of the remaining ethanol solution gave 0.344 g (95.5%) of 2-methyl-1,3-dihydroisothianaphthenium hexafluoroantimonate as white crystals. mp=126.2° C.; $^1$H-NMR (acetone-$d_6$) δ 7.39–7.55 (4 H, m, Ar—H), 4.90 (2 H, d, J=16.0 Hz, >S$^+$—CH—), 4.59 (2 H, d, J=16.0 Hz, >S$^+$—CH—), 2.71 (3 H, s, >S$^+$—CH$_3$—); $^{13}$C-NMR (acetone-$d_6$) δ 133.8, 128.3, 125.9, 48.1, 23.9.

2-Ethyl-1,3-dihydroisothianaphthenium tetrafluoroborate (B2)

Triethyloxonium tetrafluoroborate 10 ml (10 mmol; 1M solution in $CH_2Cl_2$) was added to a 10 ml dry solution of 1.326 g (10 mmol) of 1,3-dihydroisothianaphthene (Chem. Ind. (London), 1965, 1024) at 0° C. The reaction mixture was kept under $N_2$ and was stirred for 5 h. Evaporation of the solvent resulted in a black oil that crystallized upon treatment with diethyl ether. Recrystallization from ethanol gave white crystals in 53% yield. mp=75.3° C.; $^1$H-NMR (acetone-$d_6$) δ 7.4–7.6 (4 H, m, Ar—H), 5.17 (2 H, d, J=17.1 Hz, >S$^+$—CH—Ar), 4.97 (2 H, d, J=17.1 Hz, >S$^+$—CH—Ar), 3.45 (2 H, q, >S$^+$—CH$_2$—CH$_3$), 1.50 (3 H, t, >S$^+$—CH$_2$—CH$_3$); $^{13}$C-NMR (acetone-$d_6$) δ 135.05, 129.79, 126.75, 46.97, 36.76, 9.35; Anal. Calcd for $C_{10}H_{13}BF_4S$: C, 47.7%; H, 5.2%; S, 12.7%. Found: C, 47.9%; H, 5.2%; S, 12.5%.

S-methyl-2-(E-2-phenylethenyl)-[3,4]-benzo-2,5-dihydrohydrothiophenium hexafluorophosphate (B3)

To a stirred solution of lithium thiomethoxide (82.19 mmol, generated from n-BuLi and methylmercaptan) in 130 ml of ethanol/THF (2:3) 2-bromobenzylbromide (12.54 g, 50.17 mmol) was added. After 1 h of reflux 30 ml of a saturated aqueous NH4Cl solution was added. The mixture was concentrated and extracted with ether The organic phase was washed with water and dried with MgSO4. After evaporation the crude product was distilled to give a clear liquid of o-bromobenzyl methyl sulfide 9.88 g (89%).

Butyl lithium (2.96 ml, 4.61 mmol, 1.58M in hexane) was added to a 2 ml THF solution of o-bromobenzyl methyl sulfide (1.0 g, 4.61 mmol) kept at −70° C. and under N2. After 10 minutes the temperature was raised to −30° C. and kept there for 35 minutes before cinnamic aldehyde (0.61 g, 4.61 mmol) dissolved in 2 ml of THF was added. The reaction was quenched 1 h later by addition of 250 μl of water. The organic part of the reaction mixture was concentrated and CH2Cl2 was added. After washing with water the CH2Cl2 solution was dried with MgSO4, filtered and then evaporated. Flash chromatography, using CH2Cl2/petroleum ether (85:15) as eluent, yielded 0.68 g (55%) of (o-thiomethoxymethylphenyl)-E-(2-phenylethenyl)carbinol as an oil.

Hexafluorophosphoric acid (60% in water, 452 mg, 1.857 mmol) was added to a solution of (o-thiomethoxymethylphenyl)-E-(2-phenylethenyl)carbinol (251 mg, 0.928 mmol) in 4 ml of acetic acid anhydride kept at 0° C. The reaction mixture was stirred for 5 h and then the solvent was evaporated. The crude material was dissolved in CH2Cl2. This solution was washed with water, dried (MgSO4), filtered and then the solvent was evaporated to give 199 mg (54%) of brownish grey crystals of B2 as a 1.3/1 mixture of two diastereomers 1H-NMR (acetone-d6) δ major diastereomer: 7.2–7.7 (9 H, m, Ar—H), 6.74 (1H, d, J=15.8 Hz, =CH—Ph), 6.58 (1 H, dd, J=8.1 and 15.8 Hz, —CH=CH—Ph), 5.99 (1 H, d, J=8.1 Hz, —CH—CH=CH—Ph), 5.23 (1 H, d, J=16.6 Hz, >S+—CHH—), 4.70 (1 H, d, J=16.6 Hz, >S+—CHH—), 2.89 (3 H, s, CH3), minor diastereomer: 7.2–7.7 (9 H, m, Ar—H), 7.15 (1 H, d, J=15.4 Hz, =CH—Ph), 6.50 (1 H, dd, J=9.2 and 15.4 Hz, —CH=CH—Ph), 6.34 (1 H, d, J=9.2 Hz, —CH—CH=CH—Ph), 5.05 (1 H, d, J=16.1 Hz, >S+—CHH—), 4.73 (1 H, d, J=16.1 Hz, >S+—CHH—), 2.73 (3 H, s, CH3).

S-Methyl-5-phenyl-[3,4]-benzo-2,7-dihydrothiepinium hexafluorophosphate (C1)

2-(Bromomethyl)benzonitrile (20.4 g, 103 mmol) was added to suspension of lithium thiomethoxide (12.62 g, 181 mmol) in ethanol (35 mL). After the reaction mixture was refluxed for 2 h, aqueous NH4Cl (50 mL) was added. The resulting mixture was concentrated ad extracted with ether. The combined ether phase was washed with H2O and brine, dried, and concentrated to give 16.0 g (95%) of 2-(thiomethoxymethyl)-benzonitrile as a light yellow liquid.

A THF-solution of phenyl magnesium bromide (30.6 mL, 45.6 mmol) was added to 2-(thiomethoxymethyl)-benzonitrile (5.0 g, 30.6 mmol) in THF (6 mL) at ambient temperature under a N2-atmosphere. The reaction mixture was refluxed for 4 h, allowed to cool, quenched with 6M HCl (40 mL). After reflux for additional 16 h the reaction mixture was neutralized with Na2CO3 (aq. saturated) and extracted with methylene chloride. The organic phase was washed with H2O, dried, and concentrated to give a crude product which was purified by chromatography (SiO2) yielding 5.17 g (70%) of 2-(thiomethoxymethyl)-benzophenone as a light yellow liquid.

To a solution of 2-(thiomethoxymethyl)-benzophenone (2.0 g, 8.37 mmol) in THF (5 mL) was added a THF-solution of vinyl magnesium bromide (16.7 mL, 16.7 mmol) at RT under a N2-atmosphere. After reflux for 2 h, sat NH4Cl (aq) was added. Concentration followed by ether extraction yielded an organic phase which was washed with H2O, dried (MgSO4), and concentrated to give 1.79 g (77%) of phenyl(2-thiomethoxymethyl)phenyl-vinylcarbinol.

To a mixture of phenyl-(2-thiomethoxymethyl)phenyl-vinylcarbinol (1.63 g, 6 mmol) and acetic anhydride (12 mL) was added hexafluoro phosphoric acid (60% in water, 1.94 g) and the mixture was stirred for 5 h at 0° C. The mixture was concentrated and dissolved in methylene chloride. The organic phase was washed with water and NaHCO3 (aq, satur). Drying (MgSO4) and concentrated gave 1.67 g (70%) of C1 as light brown crystals. 1H-NMR (acetone-d6) δ 7.0–7.7 (9 H, m, Ar—H), 6.6 (1 H, t, J=7 Hz, =CH—), 4.63 (1 H, d, J=13 Hz, Ar—CH—), 4.26 (1 H, d, J=13 Hz, Ar—CH—), 3.82–4.05 (1 H, m, >S+—CHH—CH=), 3.3–3.5 (1 H, m, >S+—CHH—CH=), 2.85 (3 H, s, >S+—CH3—); UV-absorption max. (ethanol): 203, 239 nm.

2-Ethyl-4-oxoisothiochromanium tetrafluoroborate (D1)

1.642 g (10 mmol) isothiochroman-4-one (J. Am. Chem. Soc. 1973, 95, 2923) was alkylated with triethyloxonium tetrafluoroborate (10 mmol, 1M in methylene chloride) according to the method described for compound B2. Recrystallization in ethanol gave 1.26 g (50%) of D1 as white crystals; mp=89.6° C. 1H-NMR (acetone-d6) δ 7.65–8.14 (4 H, m, Ar—H), 5.23 (1 H, d, J=16.1 Hz, —CHH—C(O)—), 5.03 (1 H, d, J=16.1 Hz, —CHH—C(O)—), 4.80 (1 H, d, J=17.2 Hz, —CHH—Ar), 4.55 (1 H, dd, J=2.0 and 17.2 Hz, —CHH—Ar), 3.45–3.85 (2 H, m, >S+—CH2—CH3), 1.55 (3 H, t, J=7.5 Hz, >S+—CH2—CH3); 13C-NMR (acetone-d6) δ 183.64, 136.04, 131.78, 130.97, 130.75, 130.51, 128.93, 40.06, 34.45, 34.40, 8.85; UV-absorption max. (ethanol): 254, 293 nm; Anal. Calcd for C11H13BF4OS: C, 47.2%; H, 4.7%; S, 11.5%. Found: C, 47.3%; H, 4.6%; S, 11.5%.

We claim:

1. In a method of cationic polymerization of at least one cationically polymerizable monomer in the presence of a polymerization initiator, the improvement wherein said polymerization initiator is a heterocyclic, aryl substituted or with an aryl ring fused sulfonium salt with a non-nucleophilic anion, wherein the sulfonium group is positioned so that the sulfonium salt is ring-opened by activation whereby a stabilized carbocation capable of initiating cationic polymerization is formed together with a sulfide, which is covalently bonded to the cationic fragment, and which sulfonium salt has one of the following structural formulae

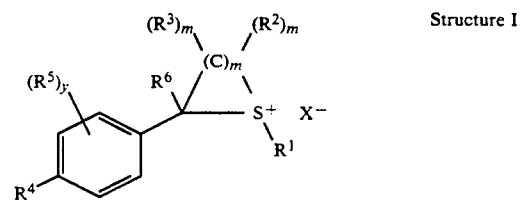

Structure I

-continued

Structure II

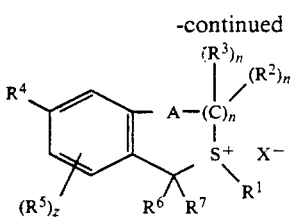

wherein
m = an integer between 3 and 5
n = an integer between 1 and 3
z = an integer between 0 and 3
y = an integer between 0 and 4
X = represents a group of the formula $MY_r(1)$ or the formula Q(2),
wherein in
$MY_r(1)$: M=Sb, As, P, B or Cl; Y represents a halogen or O and where r is an integer between 4 and 6, the formula Q(2) represents a sulfonic acid $R\text{-}SO_3$ wherein
R is an alkyl, aryl group, a halogen-substituted alkyl or a halogen-substituted aryl group,
$R^1$ represents an alkyl, cycloalkyl group, or an aryl group,
$R^2$ represents hydrogen, an alkyl, alkenyl, cycloalkenyl, cycloalkyl group, or aryl group, all $R^2$ being independent of each other,
$R^3$ represents hydrogen, an alkyl, alkenyl, cycloalkenyl, cycloalkyl group, or aryl group, all $R^3$ being independent of each other,
$R^4$ represents hydrogen, halogen, an alkenyl a cycloalkenyl, an alkyl cycloalkyl group, an alkoxy, thioalkoxy group, a hydroxyl- or alkyl ($C_1$-$C_{12}$) terminated poly(alkyleneoxide) group with up to 10 alkyleneoxide units, an aryl group, an aryloxy or thioaryloxy group,
$R^5$ represents halogen, an alkyl, cycloalkyl group, an alkoxy, thioalkoxy group, a hydroxyl- or alkyl ($C_1$-$C_{12}$) terminated poly(alkyleneoxide) group with up to 10 alkyleneoxide units, an aryl group, an aryloxy or thioaryloxy group,
wherein in structure I $R^4$ or $R^5$ (y = 1-2) also can be the group

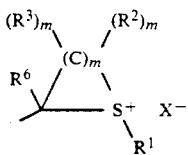

$R^6$ represents hydrogen, an alkyl, alkenyl, cycloalkenyl, cycloalkyl group, an aryl group,
$R^7$ represents hydrogen, an alkyl, alkenyl, cycloalkenyl, cycloalkyl group, or an aryl group,
A represents

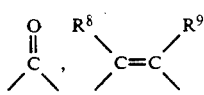

or a single bond,
$R^8$ represents hydrogen, an alkyl, cycloalkyl group, a hydroxyl- or alkyl($C_1$-$C_{12}$)terminated poly(alkyleneoxide) group with up to 10 alkyleneoxide units, an aryl group, an aryloxy or thioaryloxy group,
$R^9$ represents hydrogen, an alkyl, cycloalkyl group, hydroxyl- or alkyl($C_1$-$C_{12}$)terminated poly(alkyleneoxide) group with up to 10 alkyleneoxide units an aryl group, an aryloxy or thioaryloxy group, or
$R^8$ and $R^9$ together form an aryl ring fused with the heterocyclic sulfonium ring, said aryl ring optionally being substituted with a group $R^{10}$ which can be a halogen atom, a nitro group, an alkyl, cycloalkyl group, alkoxy, tihoalkoxy group, a hydroxyl- or alkyl($C_1$-$C_{12}$)terminated poly(alkyleneoxide) group with up to 10 alkyleneoxide units, an aryl group, an aryloxy or thioaryloxy group,
said polymerization being carried out by means of thermal activation, photochemical activation (UV-irradiation) or activation by electron bombardment (EB).

2. The method according to claim 1, wherein the sulfonium salt has the structural formula I wherein m=3, X=$MY_r$, $R^2$=H, $R^3$=H and $R^6$=H och y, $R^1$, $R^4$, $R^5$, M, Y and r are as defined in claim 1.

3. The method according to claim 2, wherein $R^4$ is

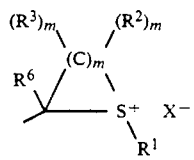

and y, $R^1$ and $R^5$ are as defined in claim 1.

4. The method according to claim 1, wherein the sulfonium salt has the structural formula

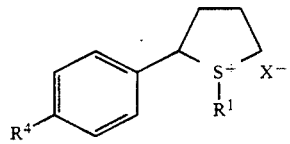

wherein $R^1$ is methyl, ethyl or n-butyl, $R^4$ is hydrogen, methyl eller methoxy and $X^-$ is $SbF_6^-$, $PF_6^-$ or $BF_4^-$.

5. The method according to claim 4, wherein the sulfonium salt is selected from
S-methyl-2-phenyltetramethylenesulfonium hexafluoroaantimonate,
S-methyl-2-phenyltetramethylenesulfonium hexafluorophosphate,
S-methyl-2-(p-tolyl)tetramethylenesulfonium hexafluoroantimonate,
S-methyl-2-(p-tolyl)tetramethylenesulfonium hexafluorophosphate,
S-methyl-2-(p-methoxyphenyl)tetramethylenesulfonium hexafluoroantimonate,
S-methyl-2-(p-methoxyphenyl)tetramethylenesulfonium hexafluorophosphate,
S-ethyl-2-phenyltetramethylenesulfonium tetrafluoroborate,
S-ethyl-2-(p-tolyl)tetramethylenesulfonium tetrafluoroborate,
S-(n-butyl)-2-phenyltetramethylenesulfonium hexafluorophosphate or
S-(n-butyl)-2-(p-methoxyphenyl)tetramethylenesulfonium hexafluorophosphate.

6. The method according to claim 1, wherein the sulfonium salt has the structural formula II wherein A is

n=1, $R^2$=H, $R^3$=H, $R^6$=H, $R^7$=H, X=$MY_r$ and z, $R^1$, $R^4$ and $R^5$, M, Y and r are as defined in claim 1.

7. The method according to claim 6, wherein the sulfonium salt is 2-ethyl-4-oxoisothiochromanium tetrafluoroborate of the structural formula

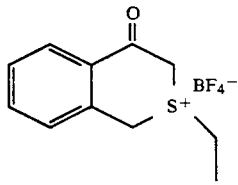

8. The method according to claim 1, wherein the sulfonium salt has the structural formula II wherein A is

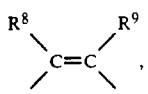

n=1, X=$MY_r$, and z, $R^1$, $R^2$, $R^3$, $R^4$, $R^5$, $R^6$, $R^7$, $R^8$, $R^9$, M, Y and r are as defined in claim 1.

9. The method according to claim 1, wherein the sulfonium salt has the structural formula II wherein A is a single bond, n=1-2, X=$MY_r$, and z, $R^1$, $R^2$, $R^3$, $R^4$, $R^5$, $R^6$, $R^7$, M, Y and r are as defined in claim 1.

10. The method according to claim 1, wherein the sulfonium salt has the structural formula

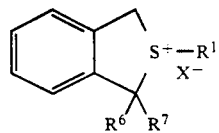

wherein $R^1$ is methyl or ethyl, $R^6$ is hydrogen or phenylethenyl, $R^7$ is hydrogen and $X^-$ is $SbF_6^-$, $PF_6^-$ or $BF_4^-$.

11. The method according to claim 10, wherein the sulfonium salt is selected from 2-methyl-1,3-dihydroisothianaphthenium hexafluoroantimonate, 2-ethyl-1,3-dihydroisothianaphthenium tetrafluoroborate eller S-methyl-2-(2-phenylethenyl)-[3,4]-benzotetrahydrothiophenium hexafluorophosphate.

12. An aryl substituted cyclic sulfonium salt of the structural formula

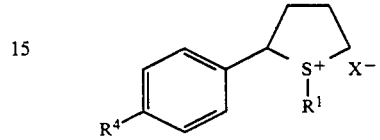

which is
S-methyl-2-phenyltetramethylenesulfonium hexafluoroaantimonate,
S-methyl-2-phenyltetramethylenesulfonium hexafluorophosphate,
S-methyl-2-(p-tolyl)tetramethylenesulfonium hexafluoroantimonate,
S-methyl-2-(p-tolyl)tetramethylenesulfonium hexafluorophosphate,
S-methyl-2-(p-methoxyphenyl)tetramethylenesulfonium hexafluoroantimonate,
S-methyl-2-(p-methoxyphenyl)tetramethylenesulfonium hexafluorophosphate,
S-ethyl-2-phenyltetramethylenesulfonium tetrafluoroborate,
S-ethyl-2-(p-tolyl)tetramethylenesulfonium tetrafluoroborate,
S-(n-butyl)-2-phenyltetramethylenesulfonium hexafluorophosphate or
S-(n-butyl)-2-(p-methoxyphenyl)tetramethylenesulfonium hexafluorophosphate.

13. The method according to claim 1 wherein,
each halogen in Y is F or Cl,
each halogen-substituted group in R is substituted by F or Cl,
each alkyl, cycloalkyl, cycloalkenyl, alkoxy or thioalkoxy group has 1-20 carbon atoms, and
the alkenyl group in $R^4$ is a vinyl group.

* * * * *